United States Patent [19]

Barnes

[11] Patent Number: 5,051,256

[45] Date of Patent: Sep. 24, 1991

[54] BIOCIDAL COMPLEX AND DRESSING FORMED THEREFROM

[76] Inventor: Carl E. Barnes, 482 Trinity Pass, New Canaan, Conn. 06840

[21] Appl. No.: 443,878

[22] Filed: Nov. 30, 1989

Related U.S. Application Data

[63] Continuation of Ser. No. 155,942, Feb. 16, 1988, abandoned, which is a continuation-in-part of Ser. No. 933,856, Aug. 15, 1978, abandoned.

[51] Int. Cl.$^5$ .................. A61K 9/00; A61F 13/00; A61L 15/00
[52] U.S. Cl. .................................... 424/402; 424/78; 424/400; 424/443; 424/445; 424/446
[58] Field of Search ............... 424/78, 667, 670, 402, 424/443, 446, 445, 400

[56] References Cited

U.S. PATENT DOCUMENTS

| | | | |
|---|---|---|---|
| 2,638,463 | 5/1953 | Ney et al. | 424/78 |
| 3,287,222 | 11/1966 | Larde et al. | 424/80 |
| 3,674,901 | 7/1972 | Shepherd et al. | 424/27 |
| 3,751,565 | 8/1973 | Santorelli | 424/150 |
| 3,764,669 | 10/1973 | Santorelli | 424/80 |
| 3,890,280 | 6/1975 | Upadhyaya | 260/78 P |
| 3,984,341 | 10/1976 | Haschke et al. | 424/150 |
| 4,113,851 | 9/1978 | Leveen et al. | 424/28 |

OTHER PUBLICATIONS

Chem. Abst. 82: 86797(t) (1975)–Kaneniwa et al.
Chem. Abst. 93: 192,048(m) (1980)–Aita et al.
Chem. Abst. 100: 86933(z) (1984)–Barnes et al.

*Primary Examiner*—Frederick E. Waddell
*Assistant Examiner*—Kevin E. Weddington
*Attorney, Agent, or Firm*—Davis Hoxie Faithfull & Hapgood

[57] ABSTRACT

A novel complex of polypyrrolidone, also known as nylon-4, and iodine is disclosed. The complex has biocidal properties exhibiting especially the fungicidal and bactericidal properties of free iodine but not its irritating and toxic properties. The complex may be formed with polypyrrolidone having any physical form, e.g. a powder, film, pulp, fiber or molded article. Bandage material made from nylon-4 fibers and complexed with iodine is a particularly useful form. Ointments and other compositions for topical application may also be made.

16 Claims, No Drawings

BIOCIDAL COMPLEX AND DRESSING FORMED THEREFROM

RELATED APPLICATIONS

This is a continuation of copending application(s) Ser. No. 07/155,942 filed on Feb. 16, 1988 now abandoned.

BACKGROUND OF THE INVENTION

The iodine complex formed by mixing polyvinylpyrrolidone (PVP) and iodine, first disclosed in U.S. Pat. No. 2,739,922 issued to Herman A. Shelanski, has established itself as the preferred way of utilizing the desirable biocidal properties of iodine while avoiding the irritating side effects. It has become the product of choice especially in surgery where it is used to coat the skin prior to incision.

PVP is a water soluble polymer and likewise the PVP-iodine complex is water soluble. There are applications however in which this solubility in water is undesirable. For example in topical applications the effectiveness of a water soluble antiseptic is of short duration since it is readily washed away not only by water but by the exudate from the wound. A water insoluble complex which slowly releases small amounts of iodine would be much more permanent and effective.

OBJECTS OF THE INVENTION

It is a primary object of this invention to provide a water insoluble and therefore more permanent complex of iodine possessing medicinal properties.

It is another object of this invention to provide a water insoluble complex of iodine which slowly releases elemental iodine in small but effective amounts over a long period of time thus prolonging the microbiological activity while minimizing the irritating side effects.

It is a further object of the invention to provide a novel bandage and suture material which in itself is the bactericidal and fungicidal agent.

It is a still further object of this invention to provide water insoluble long lasting antiseptic ointments for topical application.

Other objects will be apparent in the detailed disclosure which follows.

DESCRIPTION OF PREFERRED EMBODIMENTS

It has been found that polypyrrolidone, also known as nylon4, a polymer having the structure

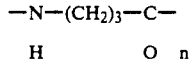

can be made to form a complex with elemental iodine which is an iodophor, exhibiting sustained release of iodine. This complex is not soluble in water, thus making it longer lasting in most applications for human and veterinary treatment.

It is surprising and unexpected that nylon-4 should form a complex with iodine since the pyrrolidone ring, which is intact in PVP, is opened and non-existent in nylon-4 which has instead a polyamide structure. Nevertheless it has been found that a complex with iodine will form very easily.

The polypyrrolidone employed to make the iodine complex may be in any physical form such as a finely divided resin, a pulp (i.e., fibrils), a molded article, a film (extruded or cast), as well as filaments for use in sutures, or textile fibers from which a fabric may be made by knitting or weaving.

The complex is best formed by immersing the nylon-4 article in a solution of iodine in aqueous potassium iodide, i.e., $KI_3$. A preferred formula is:

| Potassium iodide | 4.0 grams |
|---|---|
| Iodine | 2.0 grams |
| Water | 100 ml |

Upon immersion in this solution the white polypyrrolidone article turns to a dark chocolate-brown color almost immediately and then becomes black. Upon drying the color becomes somewhat lighter. Immersion times can range from a few seconds to about five minutes, or longer. Shorter immersion times will produce a golden yellow color in the dried article while longer times will give a dark brown color in the dried material. However the amount of iodine to be complexed is best controlled by the amount of iodine added to the complexing solution, i.e., its concentration. Up to about 20% of iodine in the complex can be added. Higher amounts of iodine will degrade the polymer and should be avoided.

The color of the dried complex is a measure of the amount of iodine present and may range from a golden yellow to a deep brown. At 20% iodine content the color is almost black. Complexes having a pale yellow color do not contain enough iodine to be effective in most applications.

The iodine complex may be formed by other methods such as exposing the nylon-4 article to iodine vapor or triturating finely ground resin powder or particles with solid iodine crystals; however immersion in the $KI_3$ solution is best.

The iodine is rather tightly held in the complex. By way of comparison, if cotton (another hydrophilic fiber) is immersed in an iodine solution prepared according to the recipe given above it develops a similar dark brown color. But the iodine is only loosely held and washes out completely with tap water within a minute. Likewise silk also develops a dark brown color but while the iodine does not wash out as readily as it does with cotton, only a tan color remains indicating but a small amount of iodine remaining in the fibers. The iodine in the dark brown complex formed with nylon-4 does not readily wash out with water. Small amounts of iodine are released however at a rate which is dependent on the temperature. The rate is very slow at room temperature but at about 100° C. it is quite rapid. For example, if the complex in the form of a fabric is placed in boiling water the iodine will be removed completely in a matter of minutes. Similarly if placed in an oven at 100° C. the iodine will sublime out of the complex very rapidly leaving a colorless nylon-4 fabric. At 40° C. no appreciable loss of iodine occurs within 24 hours. Samples may be kept for several weeks at room temperature without appreciable loss of iodine. However, when the complexed material is to be stored for longer periods of time, such as a year or more, it should be placed in a container which is impermeable to iodine vapor. Plastic bags made from a laminate of polyethylene and nylon films manufactured by Mobil Chemical company are suitable for this purpose.

In order to be effective as an antiseptic or bactericide, a slow release of iodine must occur, and at body temperature this release takes place at about the proper rate. For many reasons a bandage should be changed every 24 hours but it should remain effective during this period of time. An important feature of the nylon-4 iodine complex is that, unlike its PVP-iodine counterpart, if the bandage or other dressing gets wet, even from perspiration, the biocidal agent is not washed away.

Another embodiment of the invention is as a biocidal suture. In this application the polypyrrolidone resin is melt extruded at temperatures of about 290° C. under high pressure generated by the screw of the extruder. Care must be taken to dry the resin to not more than about 0.06% moisture content before extruding and the resin must be kept under dry nitrogen in the hopper feeding the extruder to prevent further moisture pick-up.

The molten resin is forced through a spinnerette consisting of a single hole to form a monofilament or multiple holes to form a multifilament suture. As is well known to those skilled in the art, the size of the hole and the amount of draw determine the diameter of the filament or filaments as well as the tensile strength. For certain applications a multifilament structure is preferred. In either case the suture material is then passed through an iodine bath made according to the recipe given earlier. The residence time in the bath may be from a few seconds to a few minutes depending upon the amount of iodine desired in the complex. The material is then washed in water and air dried.

For bandage applications a suitable fabric is woven or knitted from nylon-4 textile fiber and treated in the iodine bath in a similar manner.

EXAMPLE

A sample of 100% nylon-4 knit tubing weighing 11.0 grams was immersed in a 1½% iodine solution prepared as follows:

6.0 grams elemental iodine
12.0 grams of potassium iodide
400 ml water.

After 5 minutes the fabric was removed, rinsed four times with cold water and then air dried. The dried fabric was chocolate brown in color.

The fabric was tested for microbiological activities by an independent laboratory using a modified Kirby-Bauer Susceptibility Disk Diffusion Test. The only modification to the standard procedure was that the fabric was cut into squares approximately 1.5 centimeters on a side instead of the routinely used antibiotic assay discs.

The following four strains of bacteria were separately grown in Trypticase-soy broth at 35° C. until a density of 0.5 MacFarland turbidity was observed (approximately $5 \times 10^7$ organisms per milliliter): *Klebsiella pneumoniae, Pseudomonas aeruginosa, Proteus mirabilis* and *Staphylococcus aureus*. Using a sterile cotton swab, a lawn of each bacterial isolate was applied to individual 150 mm plates of Mueller-Hinton agar. Three squares of test fabric were placed on the agar surface of each plate. The plates were incubated at 35° C. for 18 hours.

The average zones of inhibition of bacterial growth as measured in millimeters from the edge of the fabric to the point of uninhibited bacterial growth were as follows:

| | |
|---|---|
| *Klebsiella pneumoniae* | 25 mm |
| *Pseudomonas aeruginosa* | 15 mm |
| *Proteus mirabilis* | 12 mm |
| *Staphylococcus aureus* | 30 mm |

The zones of inhibition are due to the diffusion of iodine from the complex into the agar rather than to the release of iodine vapor above the plate. The difference in the zones of inhibition reflects the differential sensitivity of the organisms to the iodine rather than differences in diffusion rates.

The nylon-4 iodine complex may be utilized in many other ways, for example as an inner layer in packaging to serve as a biocidal barrier thus keeping the contents of the package sterile, or as a source of a low concentration of iodine vapor to provide a sterile atmosphere. Since there are many different embodiments of this invention which may be made without departing from the spirit and scope thereof, it is to be understood that the invention is not to be limited by the above examples except as defined in the appended claims.

What is claimed is:

1. A composition having biocidal activity comprising a complex of polypyrrolidone and iodine.

2. A composition according to claim 1 wherein the polypyrrolidone is in the form of a bandage material.

3. A composition according to claim 1 wherein the polypyrrolidone is in the form of a suture.

4. A composition according to claim 1 wherein the polypyrrolidone is in the form of a finely divided powder.

5. A composition according to claim 1 wherein the polypyrrolidone is in the form of a film.

6. A composition according to claim 1 wherein the polypyrrolidone is in the form of fibrils.

7. A composition according to claim 1 wherein the polypyrrolidone is in the form of a woven fabric.

8. A composition according to claim 1 wherein the polypyrrolidone is in the form of a non-woven fabric.

9. A composition according to claim 1 in the form of a molded article.

10. A composition according to claim 1 wherein the polypyrrolidone is in the form of a fiber.

11. The composition of claim 1 in the form of an ointment.

12. The composition of claim 1 in the form of a powder.

13. An antiseptic dressing for direct application to wounds of the bodies of humans and animals which comprises a complex of polypyrrolidone and iodine.

14. The method of preparing a complex of polypyrrolidone and iodine which comprises the steps of contacting the polypyrrolidone with an aqueous solution of iodine in potassium iodide for a period of time sufficient to allow the formation of the complex, removing the polypyrrolidone from the aqueous solution and washing the polypyrrolidone with water to remove the excess potassium triiodide solution.

15. The method of claim 14 in which the temperature of the aqueous potassium iodide solution is in the range from 15° C. to 60° C.

16. The method of preparing a complex of polypyrrolidone and iodine which comprises contacting polypyrrolidone with iodine vapors.

* * * * *